United States Patent [19]

Tzikas

[11] 4,198,518
[45] Apr. 15, 1980

[54] PROCESS FOR THE PRODUCTION OF 3-SUBSTITUTED PYRAZOLANTHRONES

[75] Inventor: Athanassios Tzikas, Pratteln, Switzerland

[73] Assignee: Ciba-Geigy Corporation, Ardsley, N.Y.

[21] Appl. No.: 937,023

[22] Filed: Aug. 25, 1978

[30] Foreign Application Priority Data

Sep. 2, 1977 [CH] Switzerland ............... 10735/77
Jan. 24, 1978 [CH] Switzerland ............... 737/78

[51] Int. Cl.$^2$ .......................................... C07D 231/54
[52] U.S. Cl. ....................................................... 548/357
[58] Field of Search .............................................. 548/357

[56] References Cited

U.S. PATENT DOCUMENTS

| | | | |
|---|---|---|---|
| 1,781,248 | 11/1930 | Scheyer | 548/357 |
| 2,136,133 | 11/1938 | Hauser et al. | 548/357 |
| 2,162,201 | 6/1939 | Perkins et al. | 548/357 |

FOREIGN PATENT DOCUMENTS

| | | | |
|---|---|---|---|
| 163447 | 8/1904 | Fed. Rep. of Germany | 548/357 |
| 171293 | 8/1904 | Fed. Rep. of Germany | 548/357 |
| 2452413 | 5/1976 | Fed. Rep. of Germany | 548/357 |

OTHER PUBLICATIONS

Giua, Gazz. Chim. Italiana 1919, vol. 49 (II), pp. 166–175.
Venkataraman, The Chemistry of Synthetic Dyes, Academic Press, NY, 1952, vol. II, pp. 993–996.
Barnett, Anthracene and Antheaquinone, Bailliere, Tindall and Cox, 1921, pp. 362–365.
Woroshzow, Grundlagen der Synthese von Zwischenprodukten und Farbstoffen, Akademie Verlag, Berlin, 1966, p. 918.
Smith, The Chemistry of Open-Chain Organic Nitrogen Compounds, vol. II Benjamin, N.Y., 1966, pp. 139–140.

*Primary Examiner*—Alan L. Rotman
*Assistant Examiner*—Natalia Harkaway
*Attorney, Agent, or Firm*—Prabodh I. Almaula

[57] ABSTRACT

A process for the production of 3-substituted pyrazolanthrones of the formula

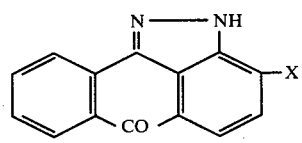

(1), wherein X is $C_1$–$C_6$ alkyl, $C_1$–$C_6$ alkoxy or a group —COR, in which R is hydrogen, $C_1$–$C_4$ alkyl, hydroxyl, $C_1$–$C_6$ alkoxy, —$NH_2$, —NH—$C_1$–$C_6$ alkyl or —$NR_1R_2$, in which $R_1$ and $R_2$, each independently of the other, are $C_1$–$C_6$ alkyl, which comprises reacting 1-nitroanthraquinones of the formula

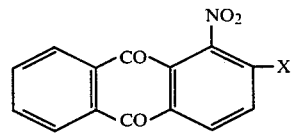

(2), wherein X is as defined in formula (1), in aprotic dipolar solvents, with hydrazine or hydrazine hydrate, at normal or slightly elevated temperature, to give 3-substituted pyrazolanthrones of the formula (1).

2 Claims, No Drawings

PROCESS FOR THE PRODUCTION OF 3-SUBSTITUTED PYRAZOLANTHRONES

The present invention relates to a process for the production of 3-substituted pyrazolanthrones of the formula

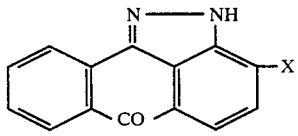

wherein X is $C_1$–$C_6$ alkyl, $C_1$–$C_6$ alkoxy or a group —COR, in which R is hydrogen, $C_1$–$C_4$ alkyl, hydroxyl, $C_1$–$C_6$ alkoxy, —$NH_2$, —NH—$C_1$–$C_6$ alkyl or —$NR_1R_2$, in which $R_1$ and $R_2$, each independently of the other, are $C_1$–$C_6$ alkyl, which comprises reacting 1-nitroanthraquinones of the formula

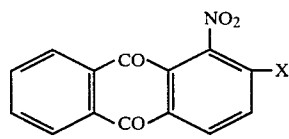

wherein X is as defined in formula (1), in aprotic dipolar solvents, with hydrazine or hydrazine hydrate, at normal or slightly elevated temperature, to give 3-substituted pyrazolanthrones of the formula (1).

The substituent X in formulae (1) and (2) can be for example: methyl, ethyl, propyl, isopropyl, butyl, hexyl, methoxy, ethoxy, propoxy, isopropoxy, butoxy, formyl, acetyl, propionyl, carboxyl, methoxycarbonyl, ethoxycarbonyl, propoxycarbonyl, carbamoyl, N-methylcarbamoyl, N-ethylcarbamoyl, N,N-dimethylcarbamoyl and N,N-diethylcarbamoyl.

As starting compounds of the formula (2), there may be mentioned in particular: 1-nitro-2-methylanthraquinone, 1-nitro-2-ethylanthraquinone and 1-nitro-2-carboxyanthraquinone.

Examples of suitable aprotic dipolar solvents which may be used in the process of the invention are: N-methyl-2-pyroolidone, tetramethylurea, sulfolane, hexamethylphosphoric triamide, dimethyl sulfoxide, dimethyl acetamide, diethyl acetamide, acetonitrile, dimethyl formamide, 3,3'-thiodipropionitrile and also pyridine.

The most advantageous reaction temperature depends on the starting compounds and the solvent employed. Thus the reaction can often be carried out at room temperature. During the reaction, the temperature of the reaction mixture generally rises to 30° to 40° C. The reaction can also be initiated above room temperature (e.g. at 30° C.) or below it (e.g. at 5° to 10° C.). The advantageous temperature range for the process of the invention is that between about 0° and 100° C.

A preferred embodiment of the process of the invention consists in reacting 1-nitro-2-methylanthraquinone, 1-nitro-2-ethylanthraquinone or 1-nitro-2-carboxyanthraquinone in N-methyl-2-pyrrolidone, sulfolane or dimethyl sulfoxide with hydrazine hydrate, to give 3-methylpyrazolanthrone, 3-ethylpyrazolanthrone or 3-carboxypyrazolanthrone.

In the course of the process of the present invention, there is probably formed as intermediate the corresponding 2-substituted 1-hydrazinoanthraquinone, which is immediately cyclised to the pyrazolanthrone.

The 3-substituted pyrazolanthrones of the formula (1) are important intermediates for the production of valuable vat dyes, pigments and disperse dyes.

The invention is illustrated by the following Examples in which the parts are by weight.

EXAMPLE 1

16 Parts of 1-nitro-2-methylanthraquinone are suspended in 140 parts of N-methyl-2-pyrrolidone. The suspension is heated to 85° C. and, at this temperature, a solution of 3.2 parts of hydrazine hydrate in 40 parts of N-methyl-2-pyrrolidone are added dropwise in the course of 20 minutes. The reaction mixture is then stirred for 5 minutes, cooled to room temperature and filtered. The filter residue is non-reacted starting material (3 parts). Water is added to the filtrate, which is then filtered. The residue is washed neutral with water. Yield: 12 parts of 3-methyl-pyrazolanthrone of the formula

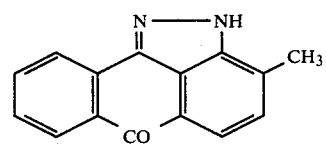

EXAMPLE 2

10 Parts of 1-nitro-2-ethylanthraquinone are suspended at room temperature in 50 parts of sulfolane. The suspension is heated to 55° C. and, at this temperature, 4 parts of hydrazine, dissolved in 20 parts of sulfolane, are added dropwise in the course of 2 hours. The reaction mixture is stirred for 10 minutes and filtered after the addition of 200 parts of a mixture of ice and water. The filter cake is washed neutral with water. Yield: 9 parts of 3-ethylpyrazolanthrone of the formula

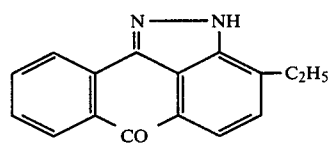

EXAMPLE 3

10 Parts of 1-nitro-2-ethylanthraquinone are suspended at room temperature in 50 parts of N-methyl-2-pyrrolidone. The suspension is heated to 60° C. and, at this temperature, 4 parts of hydrazine hydrate, dissolved in 20 parts of N-methyl-2-pyrrolidone, are added dropwise in the course of 2 hours. The reaction mixture is stirred for 10 minutes and filtered after the addition of 200 parts of a mixture of ice and water. The filter cake is washed neutral with water. Yield: 8.5 parts of 3-ethylpyrazolanthrone of the formula (4).

EXAMPLE 4

10 Parts of 1-nitro-2-ethylanthraquinone are suspended at room temperature in 60 parts of sulfolane. Then 4 parts of hydrazine hydrate, dissolved in 20 parts of sulfolane, are added dropwise to this suspension in the course of 2 hours. The reaction mixture is then stirred for 10 minutes and filtered after the addition of 200 parts of a mixture of ice and water. The filter cake is washed neutral with water. Yield: 8.5 parts of 3-ethylpyrazolanthrone of the formula (4).

EXAMPLE 5

10 Parts of 1-nitro-2-ethylanthraquinone are suspended at room temperature in 60 parts of N-methyl-2-pyrrolidone. Then 4 parts of hydrazine hydrate, dissolved in 20 parts of N-methyl-2-pyrrolidone, are added dropwise to this suspension in the course of 2 hours. The reaction mixture is then stirred for 10 minutes and filtered after the addition of 200 parts of a mixture of ice and water. The filter cake is washed neutral with water. Yield: 8.2 parts of 3-ethylpyrazolanthrone of the formula (4).

EXAMPLE 6

10 Parts of 1-nitro-2-ethylanthraquinone are suspended at room temperature in 50 parts of dimethyl sulfoxide. The suspension is heated to 55°–60° C. and, at this temperature, 4 parts of hydrazine hydrate, dissolved in 200 parts of dimethyl sulfoxide, are added dropwise in the course of 2 hours. The reaction mixture is then stirred for 10 minutes and filtered after the addition of 200 parts of a mixture of ice and water. The filter cake is washed neutral with water. Yield: 9 parts of 3-ethylpyrazolanthrone of the formula (4).

EXAMPLE 7

10 Parts of 1-nitro-2-carboxyanthraquinone are suspended at room temperature in 50 parts of sulfolane. The suspension is heated to 55° C. and, at this temperature, 4 parts of hydrazine hydrate, dissolved in 20 parts of sulfolane, are added dropwise in the course of 2 hours. The reaction mixture is stirred for 10 minutes and filtered after the addition of 200 parts of a mixture of ice and water. The filter cake is washed neutral with water. Yield: 9 parts of 3-carboxypyrazolanthrone of the formula

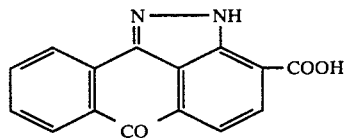

(5).

EXAMPLE 8

10 Parts of 1-nitro-2-carboxyanthraquinone are suspended at room temperature in 50 parts of N-methyl-2-pyrrolidone. The suspension is heated to 50° C. and, at this temperature, 4 parts of hydrazine hydrate, dissolved in 20 parts of N-methyl-2-pyrrolidone, are added dropwise in the course of 2 hours. The reaction mixture is then stirred for 10 minutes and filtered after the addition of 200 parts of a mixture of ice and water. The filter cake is washed neutral with water. Yield: 8.5 parts of 3-carboxypyrazolanthrone of the formula (5).

EXAMPLE 9

10 Parts of 1-nitro-2-carboxyanthraquinone are suspended at room temperature in 60 parts of N-methyl-2-pyrrolidone. Then 4 parts of hydrazine hydrate, dissolved in 20 parts of N-methyl-2-pyrrolidone, are added dropwise to this suspension in the course of 2 hours. The reaction mixture is stirred for 10 minutes and filtered after the addition of 200 parts of a mixture of ice and water. The filter cake is washed neutral with water and dried. Yield: 8.4 parts of 3-carboxypyrazolanthrone of the formula (5).

EXAMPLE 10

10 Parts of 1-nitro-2-carboxyanthraquinone are suspended at room temperature in 60 parts of sulfolane. Then 4 parts of hydrazine hydrate, dissolved in 20 parts of sulfolane, are added dropwise to this suspension in the course of 2 hours. The reaction mixture is then stirred for 10 minutes and filtered after the addition of 200 parts of a mixture of ice and water. The filter cake is washed neutral with water. Yield: 8.6 parts of 3-carboxypyrazolanthrone of the formula (5).

EXAMPLE 11

10 Parts of 1-nitro-2-carboxyanthraquinone are suspended at room temperature in 50 parts of dimethyl sulfoxide. The suspension is heated to 55°–60° C. and at this temperature 4 parts of hydrazine hydrate, dissolved in 20 parts of dimethyl sulfoxide, are added dropwise to this suspension in the course of 2 hours. The reaction mixture is then stirred for 10 minutes and filtered after the addition of 200 parts of a mixture of ice and water. The filter cake is washed neutral with water. Yield: 9 parts of 3-carboxypyrazolanthrone of the formula (5).

What is claimed is:
1. A process for the production of 3-substituted pyrazolanthrone of the formula

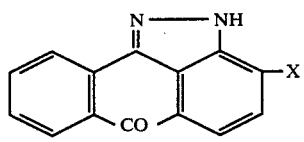

(1), wherein X is $C_1$–$C_6$ alkyl, $C_1$–$C_6$ alkoxy or a group —COR, in which R is hydrogen, $C_1$–$C_4$ alkyl, hydroxyl, $C_1$–$C_6$ alkoxy, —$NH_2$, —NH—$C_1$–$C_6$ alkyl or —$NR_1R_2$, in which $R_1$ and $R_2$, each independently of the other, are $C_1$–$C_6$ alkyl, which comprises reacting 1-nitroanthraquinone of the formula

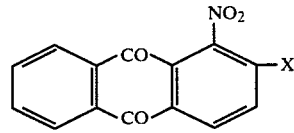

(2), wherein X is as defined in formula (1), in aprotic dipolar solvent, with hydrazine or hydrazine hydrate, at normal or slightly elevated temperature, to give 3-substituted pyrazolanthrone of the formula (1).

2. A process according to claim 1, wherein 1-nitro-2-methylanthraquinone, 1-nitro-2-ethylanthraquinone or 1-nitro-2-carboxyanthraquinone is reacted in N-methyl-2-pyrrolidone, sulfolane or dimethyl sulfoxide, with hydrazine hydrate, to give 3-methylpyrazolanthrone, 3-ethylpyrazolanthrone or 3-carboxypyrazolanthrone.

* * * * *

UNITED STATES PATENT AND TRADEMARK OFFICE
CERTIFICATE OF CORRECTION

PATENT NO. : 4,198,518
DATED : April 15, 1980
INVENTOR(S) : Athanassios Tzikas

It is certified that error appears in the above-identified patent and that said Letters Patent are hereby corrected as shown below:

Cover page under [73] Assignee: "Ciba-Geigy Corporation, Ardsley, N.Y."

should be deleted.

*Signed and Sealed this*

*Eighteenth* Day of *November 1980*

[SEAL]

*Attest:*

*Attesting Officer*

SIDNEY A. DIAMOND

*Commissioner of Patents and Trademarks*